(12) United States Patent
Cheng

(10) Patent No.: US 6,856,394 B2
(45) Date of Patent: Feb. 15, 2005

(54) SYSTEM FOR MONITORING OXIDANT CONCENTRATION OF SLURRY IN A CHEMICAL MECHANICAL POLISHING PROCESS

(75) Inventor: Chi-Feng Cheng, Yuan-Lin Cheng (TW)

(73) Assignee: Macronix International Co., Ltd., Hsinchu (TW)

( * ) Notice: Subject to any disclaimer, the term of this patent is extended or adjusted under 35 U.S.C. 154(b) by 349 days.

(21) Appl. No.: 10/104,330

(22) Filed: Mar. 22, 2002

(65) Prior Publication Data

US 2002/0171837 A1 Nov. 21, 2002

(30) Foreign Application Priority Data

May 17, 2001 (TW) .......................................... 90111791 A

(51) Int. Cl.⁷ .............................................. G01N 21/59
(52) U.S. Cl. ...................................................... 356/436
(58) Field of Search .............................. 356/246, 440, 356/342, 436, 601, 630, 632, 336; 451/1–8, 285–289; 438/691–692; 156/345

(56) References Cited

U.S. PATENT DOCUMENTS 6,267,641 B1 * 7/2001 Vanell et al. .................. 451/6
6,517,413 B1 * 2/2003 Hu et al. ....................... 451/6

* cited by examiner

Primary Examiner—Tu T. Nguyen
(74) Attorney, Agent, or Firm—J.C. Patents

(57) ABSTRACT

A system for monitoring oxidant concentration in a chemical mechanical polishing process, including a spectrometer and a central controller. The spectrometer is coupled to a conduit for supplying slurry between a slurry supply tub and a polishing table. The spectrometer is used to detect the oxidant concentration of the slurry. The central controller is coupled to the spectrometer, the slurry supply tub and the polishing table. The central controller is used to adjust the composition of the slurry in the slurry supply tub and the polishing condition of the polishing table according to the oxidant concentration of the slurry obtained from a signal transmitted by the spectrometer.

19 Claims, 1 Drawing Sheet

SYSTEM FOR MONITORING OXIDANT CONCENTRATION OF SLURRY IN A CHEMICAL MECHANICAL POLISHING PROCESS

CROSS-REFERENCE TO RELATED APPLICATION

This application claims the priority benefit of Taiwan application serial No. 90111791, filed May 17, 2001.

BACKGROUND OF THE INVENTION

1. Field of the Invention

The invention relates in general to a monitoring system for a semiconductor process. More particularly, the invention relates to a system for monitoring an oxidant concentration in a chemical mechanical polishing (CMP) process.

2. Description of the Related Art

Among the various kinds of planarization processes, chemical mechanical polishing is one of the most straightforward and fastest techniques. Chemical mechanical polishing process is frequently used because it can achieve global planarization. In the chemical mechanical polishing process, a substrate is pressed on a rotating polishing pad. The surface of the substrate is planarized by the polishing pad with the aid of a slurry that contains polishing particles. When the surface to be polished includes a metal layer or an organic polymer layer, an oxidant is added into the slurry, so that the surface is more easily polished and removed.

In the chemical mechanical polishing process, the polishing rate of the substrate is basically proportional to four factors. These four factors include the rotation speed of the polishing pad, the pressure applied to the substrate by the polishing pad, the oxidant concentration of the slurry. The above factors need to be monitored and adjusted according to process requirements to insure that the thickness removed from the polished layer meets the predetermined value.

In the prior art, the oxidant concentration of a slurry is detected using a titration method. That is, a reductive is titrated with the oxidant of the slurry, and another agent is further used to detect the endpoint of titration. This detection method is slow and requires a lot of chemical agents, incurring a long process time, a high cost and labor. Furthermore, as the determination speed of the oxidant concentration is slow, the polishing condition of the polishing table cannot be adjusted in a real time, so that a constant polishing rate cannot be obtained. The thickness removed is thus non-uniform to cause quality difference for products.

SUMMARY OF THE INVENTION

The invention provides a monitoring system for oxidant concentration of a slurry. The monitoring system comprises a spectrometer and a central controller. The spectrometer is coupled to the conduit for supplying a slurry between the slurry supply tub and a polishing table. The spectrometer uses an optical method to detect the oxidant concentration of the slurry. The central controller is connected to the spectrometer, the slurry supply tub and the polishing table. According to the oxidant concentration obtained from a signal transmitted from the spectrometer, the central controller adjusts the composition of the slurry in the slurry supply tub and the polishing condition of the polishing table.

The invention further provides a chemical mechanical polishing system with a real time adjustment. The chemical mechanical polishing system includes a polishing supply tub, a polishing table, a conduit, a spectrometer and a central controller. The slurry supply tub is used to carry a slurry of which the composition comprises an oxidant. The polishing table comprises a polishing pad to polish a substrate. The conduit is used to transport the slurry from the slurry supply tub to the polishing table. The spectrometer is coupled to the conduit and uses an optical method to detect the oxidant concentration of the slurry. The central controller is connected to the spectrometer, the slurry supply tub and the polishing table. The composition of the slurry and the polishing condition of the polishing table are adjusted by the central controller according to the oxidant concentration of the slurry obtained from a signal transmitted from the spectrometer.

The invention uses a spectrometer to detect the oxidant concentration of a slurry by an optical method. Therefore, the chemical agents used in conventional titration method are no longer required. Maintenance cost and labor can be saved. Since the invention instantly detects the oxidant concentration of a slurry, a constant polishing speed is maintained by a real time adjustment of the polishing condition of the polishing table.

Both the foregoing general description and the following detailed description are exemplary and explanatory only and are not restrictive of the invention, as claimed.

DESCRIPTION OF THE PREFERRED EMBODIMENTS

Figure 1:
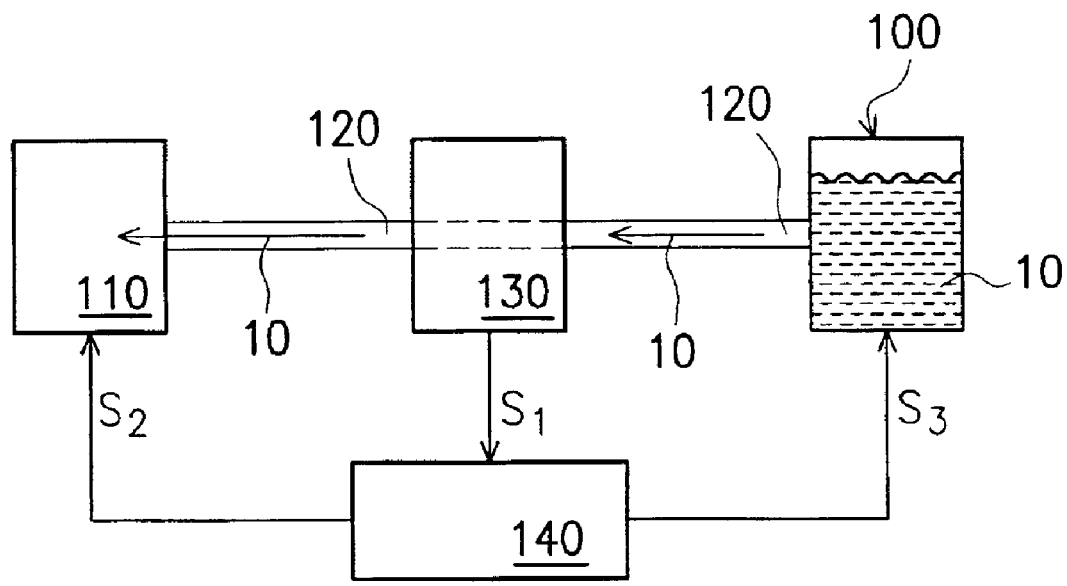
FIG. 1 shows a monitoring system for oxidant concentration of a slurry used in a chemical mechanical polishing system according to the present invention.

Referring to FIG. 1, a monitoring system for oxidant concentration of a slurry in a chemical mechanical polishing system according to the present invention is shown. In FIG. 1, the chemical mechanical polishing system comprises a slurry supply tub 100, a polishing table 110, a conduit 120, a spectrometer 130 and a central controller 140.

In FIG. 1, the slurry supply tub 100 is used to carry a slurry 10 that contains an oxidant, such as perhydrol, iron salt ($Fe^{+3}$ salt) for polishing metal, or potassium ferricyanide $K_3Fe(CN)_6$. The conduit 120 is used to convey the slurry 10 from the slurry supply tub 100 to the polishing table 110. The spectrometer 130 is connected to the conduit 120 and uses an optical method to detect the oxidant concentration of the slurry 10. The spectrometer 130 includes an absorption spectrometer, preferably, an UV/visible light absorption spectrometer with a wavelength ranged from about 200 nm to about 1000 nm. The spectrometer 130 also includes a Raman spectrometer that detects a spectrum of the reflection of a light source. The X-axis indicates the wavelength difference spectrum of the light source and the reflected light. The polishing table 110 comprises a polishing pad (not shown) thereon. With the aid of the slurry 10 conveyed by the conduit 120, a substrate (not shown) is polished by the polishing pad.

The central controller 140 is the heart of the monitoring system for oxidant concentration of the slurry in the invention. As shown in FIG. 1, the central controller 140 is connected to the spectrometer 130, the slurry supply tub 100 and the polishing table 110. The central controller 140 receives a signal $S_1$ for absorption level or light intensity transmitted from the spectrometer 140, and calculates the oxidant concentration of the slurry 10 according to the signal $S_1$. According to the oxidant concentration, a control signal $S_2$ is sent to the polishing table 110 from the central controller 140 to adjust the rotation speed and/or the pressure applied to the substrate to be polished. Or alternatively, the central controller 140 outputs another controller signal $S_3$ to the slurry supply tub 110, which is then ordered to adjust the oxidant concentration or/and the number of polishing particles per unit volume of the slurry therein. Of course, the central controller 140 may output the control signals $S_2$ and $S_3$ at the same time. For example, when the central controller 140 determines that the oxidant concentration of the slurry 10 is too high, the rotation speed of the polishing pad, the pressure applied to the substrate, or the number of polishing particles of the slurry can be reduced to maintain a constant polishing rate. Or alternatively, by directly reducing the additive proportion of the oxidant, the oxidant concentration of the slurry can also be reduced.

Figure 2:
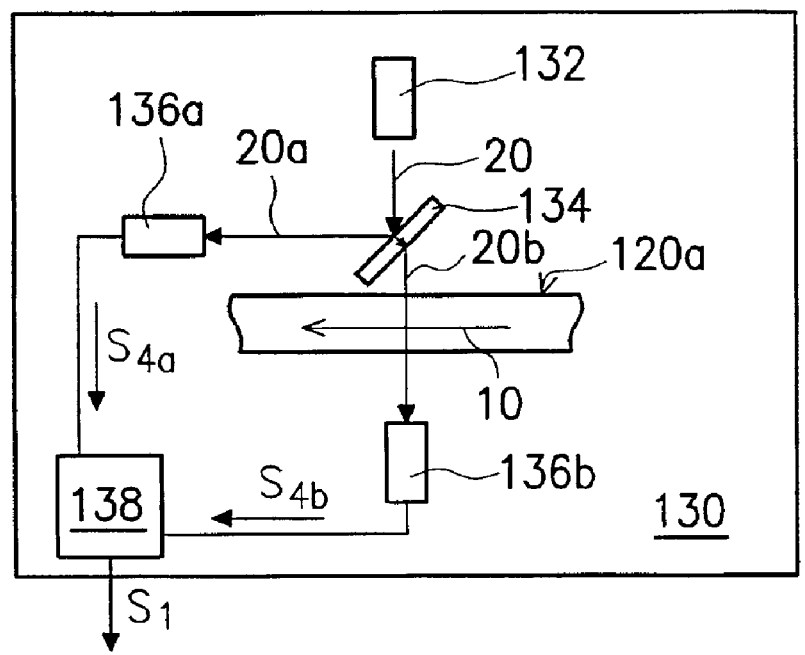
FIG. 2 shows the structure and operation theory of an absorption spectrometer used in the chemical mechanical polishing system according to the invention.

In FIG. 2, the structure and operation theory of the spectrometer 130 used in the chemical mechanical polishing system is shown. The spectrometer 130 includes an absorption spectrometer. As shown in FIG. 2, a light beam 20 is emitted from a light source 130 of the spectrometer 130. Preferably, the light source has a wavelength at the absorption peak of the oxidant of the slurry 10 to reduce the deviation of concentration measurement. The light beam 20 is split into two beams 20a and 20b after the splitter 134. The light beam 20a is absorbed by the photodetector 136a by which a light intensity is detected as a reference. The light beam 20b travels through a translucent conduit 120a (a part of the conduit 120) and is absorbed by the slurry 10 that flows through the translucent conduit 120a. The light beam 20b is then absorbed by the photodetector 136b. The light intensity $S_{4b}$ obtained by the photodetector 136b and the light intensity $S_{4a}$ obtained by the photodetector 136a are then input to a comparator 138 for comparison. The absorption intensity of the slurry 10 can thus be obtained. A signal $S_1$ of absorption intensity is output from the spectrometer 130. According to the signal $S_1$, the oxidant concentration of the slurry can be obtained.

In the above embodiment, the invention uses an absorption spectrometer to detect the oxidant concentration of a slurry using an optical method. The fast detection of the oxidant concentration of the slurry used in a chemical mechanical polishing system allows a real time adjustment of the chemical mechanical polishing system, such that the polishing speed is constant and product uniformity can be obtained. In addition, manual titration is not used, so that the chemical agents used in the invention are saved, lowering cost and labor.

Other embodiments of the invention will appear to those skilled in the art from consideration of the specification and practice of the invention disclosed herein. It is intended that the specification and examples be considered as exemplary only, with a true scope and spirit of the invention being indicated by the following claims.

What is claimed is:

1. A monitoring system for oxidant concentration of a slurry used in a chemical mechanical polishing system, the chemical mechanical polishing system comprising a slurry supply tub, a conduit and a polishing table, wherein the slurry is provided from the slurry supply tub to the polishing table through the conduit, the monitoring system comprising:

a spectrometer, connected to the conduit to detect the oxidant concentration of the slurry using an optical method; and a central controller, connected to the spectrometer, the slurry supply tub and the polishing table, wherein the central controller adjusts a composition of the slurry and a polishing condition of the polishing table according to the oxidant concentration obtained from a signal transmitted from the spectrometer.

2. The monitoring system according to claim 1, wherein the spectrometer comprises an absorption spectrometer.

3. The monitoring system according to claim 2, wherein the absorption spectrometer comprises an UV or visible light absorption spectrometer.

4. The monitoring system according to claim 3, wherein a measuring wavelength of the UV or visible light absorption spectrometer ranges from about 200 nm to about 1000 nm.

5. The monitoring system according to claim 1, wherein composition of the slurry adjusted by the central controller includes the oxidant concentration.

6. The monitoring system according to claim 1, wherein the polishing table uses a polishing pad thereon to polish a substrate, and the polishing condition includes a rotation speed of the polishing pad.

7. The monitoring system according to claim 1, wherein the polishing table uses a polishing pad thereon to polish a substrate, and the polishing condition includes a pressure applied to the substrate.

8. The monitoring system according to claim 1, wherein the oxidant comprises perhydrol.

9. The monitoring system according to claim 1, wherein the oxidant comprises iron salt.

10. A chemical mechanical polishing system with a real time adjustment, comprising:

a slurry supply tub, to carry a slurry comprising an oxidant;

a polishing table, with a polishing pad thereon to polish a substrate;

a conduit, to transport the slurry from the slurry supply tub to the polishing table;

a spectrometer, connected to the conduit and using an optical method to detect an oxidant concentration of the slurry; and a central controller, connected to the spectrometer, the slurry supply tub and the polishing table, the central controller adjusting a composition of the slurry and a polishing condition of the polishing table according to the oxidant concentration obtained from a signal transmitted from the spectrometer.

11. The chemical mechanical polishing system according to claim 10, wherein the spectrometer comprises an absorption spectrometer.

12. The chemical mechanical polishing system according to claim 11, wherein the absorption spectrometer comprises an UV or visible light absorption spectrometer.

13. The chemical mechanical polishing system according to claim 12, wherein a measuring wavelength of the UV or visible light absorption spectrometer ranges from about 200 nm to about 1000 nm.

14. The chemical mechanical polishing system according to claim 10, wherein the composition of the slurry comprises a polishing particle, and the composition of the slurry adjusted by central controller includes a number of the polishing particles in the slurry.

15. The chemical mechanical polishing system according to claim 10, wherein composition of the slurry adjusted by the central controller includes the oxidant concentration.

16. The chemical mechanical polishing system according to claim 10, wherein the polishing table uses a polishing pad thereon to polish a substrate, and the polishing condition includes a rotation speed of the polishing pad.

17. The chemical mechanical polishing system according to claim 10, wherein the polishing table uses a polishing pad thereon to polish a substrate, and the polishing condition includes a pressure applied to the substrate.

18. The chemical mechanical polishing system according to claim 10, wherein the oxidant comprises perhydrol.

19. The chemical mechanical polishing system according to claim 10, wherein the oxidant comprises iron salt.

* * * * *